United States Patent [19]

Howarth et al.

[11] Patent Number: 4,812,572

[45] Date of Patent: Mar. 14, 1989

[54] PROCESS FOR PREPARATION OF FLUOROAROMATIC OR FLUOROHETEROCYCLIC COMPOUNDS

[75] Inventors: Michael S. Howarth, Littleborough; David M. Tomkinson, Rochdale, both of England

[73] Assignee: Imperial Chemical Industries PLC, London, England

[21] Appl. No.: 77,875

[22] Filed: Jul. 27, 1987

[30] Foreign Application Priority Data

Aug. 8, 1986 [GB] United Kingdom ............... 8619375

[51] Int. Cl.$^4$ ............... C07D 211/72; C07D 211/84; C07D 213/72; C07D 211/90
[52] U.S. Cl. .................................. 546/290; 546/345; 546/312; 546/307; 546/296; 546/318; 546/321; 546/326; 570/141
[58] Field of Search ............... 546/345, 312, 307, 296, 546/290, 318, 321, 326; 570/141

[56] References Cited

U.S. PATENT DOCUMENTS

| | | | |
|---|---|---|---|
| 3,798,228 | 3/1974 | Boudakian et al. | 546/345 |
| 4,075,252 | 2/1978 | Boudakian | 546/345 |
| 4,096,196 | 6/1978 | Boudakian | 546/345 |
| 4,194,054 | 3/1980 | Forster et al. | 546/345 |

FOREIGN PATENT DOCUMENTS 1360327 7/1974 United Kingdom ............... 546/345

*Primary Examiner*—Mary C. Lee
*Assistant Examiner*—Robert C. Whittenbaugh
*Attorney, Agent, or Firm*—Cushman, Darby & Cushman

[57] ABSTRACT

A process for the preparation of a fluoroaromatic or fluoroheterocyclic compound, which comprises diazotizing the corresponding amino-aromatic or amino-heterocyclic compound in hydrogen fluoride and decomposing the diazonium salt in the diazotization mixture so formed, characterized in that decomposition is carried out at super atmospheric pressure.

15 Claims, 1 Drawing Sheet

PROCESS FOR PREPARATION OF FLUOROAROMATIC OR FLUOROHETEROCYCLIC COMPOUNDS

This invention relates to the preparation of fluoroaromatic and fluoroheterocyclic compounds. In particular it relates to the preparation of fluorobenzene and fluoropyridine compounds.

It is known that fluorobenzene and substituted fluorobenzenes can be prepared by diazotising the appropriate aminobenzene in anhydrous hydrogen fluoride and decomposing the benzenediazonium fluoride so formed. Decomposition is carried out by heating the diazonium salt until all nitrogen has been removed. This may occur by the time the temperature reaches the reflux temperature of the diazotisation mixture. However, where the amine is one substituted in an ortho position with an electron-withdrawing group, the yields obtained using this process are unsatisfactory.

It has now been found that yields obtained can be increased up to as much as 90% or more if the decomposition of the diazonium fluoride is effected at superatmospheric pressure. The usual method of achieving high boiling hydrogen fluoride is to add watr to the reaction system. This elevates the temperature to that at which decomposition takes place. However undesirable products of hydrolysis such as salicylic acid leads to lower yields of the desired, 2-fluorobenzoic acid. This is described in detail in Research Disclosure 1984 No 24704. This is particularly so where the amine is one having either a carboxyl group or other electron-withdrawing group for example at a position ortho to the amine group diazotised.

This striking beneficial result obtained by the use of increased pressure although an apparently simple modification of the processes of the prior art is, in fact, surprising. One of the major items of prior art in this field is the paper by Ferm et al, JACS 72 4809 (1950) which describes an investigation of the general applicability of the process involving decomposition of benzene diazonium fluorides for the preparation of fluorobenzenes. This paper discloses, for example, that when the process is applied to the preparation of 0-fluorobenzoic acid the yield obtained is only 57%. Similarly, when the process is applied to other amines substituted in the ortho position with a group which contains one or more atoms having an unshared electron pair the result was an unsatisfactory yield of the desired fluoro compound. These other amines were 0-chloroaniline, 0-nitroaniline, 0-aminophenol and 0-anisidine. In each of these cases little nitrogen was evolved during the attempted decomposition of the corresponding diazonium fluoride, and failure of the synthesis apparently resulted from the fact that the diazonium salt was not decomposed at the highest temperature obtainable in anhydrous hydrogen fluoride under reflux at atmospheric pressure. The applicants have atempted to confirm the results disclosed by Ferm et al and found the yields of the desired product not just to be unsatisfactory but to be totally unacceptable for use in a manufacturing process. The Applicants have attempted by way of comparison to make 1,2 difluorobenzene from 2-fluoroaniline by the general method given by Ferm et al, the result of which is described in Example 8.

The Ferm paper further discloses that the attempted decomposition of the diazonium fluorides at higher temperatures under pressure led to the formation of a complex mixture of high melting solids. This statement is a clear warning of the results to be expected when the decomposition of diazonium fluoride is attempted under super atmospheric pressure.

Although Ferm does not fully describe the procedure adopted for the attempted decomposition of the diazonium fluorides under super atmospheric pressure the disclosure clearly teaches the skilled man away from this process.

However, it has now been found according to a preferred embodiment of the present invention that excellent yields of 2-fluorobenzoic acid and other fluoro aromatic compounds can be obtained.

The pressure (whether autogenous or otherwise) applied to the hydrogen fluoride composition containing the diazonium fluoride salt must be sufficient to raise the boiling point of that composition to a temperature above the lowest practicable temperature at which the salt can be decomposed in a reasonable amount of time. The precise conditions adopted, therefore, will depend to a substantial extent on the particular diazonium salt to be decomposed. However, in general, we have found that suitable temperatures lie in the range from 40° C. to 100° C., preferably 60° C. to 100° C., especially 70° C. to 90° C. and especially in the range 75° C. to 85° C. The last mentioned range being particularly suitable for the decomposition of benzene diazonium fluoride-2-carboxylate.

The super atmospheric pressure used in the process of this invention depends upon the decomposition temperature (or temperature range) at which the diazonium fluoride decomposes. The minimum pressure used should raise the boiling point of the hydrogen fluoride reaction system to the decomposition temperature (or above) of the diazonium fluoride.

Where the pressure is autogenous it has two components: first, the vapour pressure of the hydrogen fluoride and, secondly, the pressure of the nitrogen which results from the decomposition of the diazonium fluoride. With a view to keeping the pressure to a conveniently low value it has been found convenient, according to the present invention, to remove some or all of the evolved nitrogen so that the pressure in the reaction chamber is less than would be the case if all the evolved nitrogen were present. Where, for example, the diazonium fluoride is benzene diazonium fluoride-2-carboxylate and substantially all the evolved nitrogen is removed continuously from the reaction chamber, it has been found in general that a suitable pressure is in the range 70–200 psig, preferably in therange 80 to 100 psig especially 90 or other value in the range 85 to 95 psig. In commercial plant there may be cost savings in operating at the relatively lower pressures which may be obtained in this way.

However, where evolved nitrogen is not removed the corresponding pressure in a closed reaction chamber is generally in the range 200 to 500, preferably 200 to 300, especially substantially 250 or other value in the range 220 to 280 psig.

The accompanying drawing shows a graph of temperature against vapour pressure of anhydrous hydrogen fluoride. From this relationship can be ascertained the appropriate pressure required in the process of the invention. For example, where the diazonium fluoride is one having a sharp decomposition temperature, the pressure corresponding to that temperature can then be used in the process of the invention. If, in practice, the temperature of the hydrogen fluoride reaction mixture under that pressure is not sufficiently high to result in decomposition of the diazonium fluoride an appropriate change can be made.

It should be noted that in the graph the pressure coordinate is expressed in psi absolute units.

Diazotisation of the amine may be carried out using any suitable diazotising agent. Conveniently the agent is formed in situ, for example by dissolving an alkali metal nitrite, for instance sodium nitrite, in excess hydrogen fluoride. Normally, at least 1 mole of diazotising agent per mole of the amine will be used, preferably from 1 to 1.25 moles, and typically about 1.1 moles. The temperature of diazotisation is not critical: a temperature from −5° C. to 20° C. is satisfactory and is conveniently room temperature. Any excess diazotising agent remaining may be destroyed by the addition of urea or sulphamic acid.

Hydrogen fluoride provides a source of fluorine and forms at least part of the reaction medium. It will also normally be used to prepare the diazotising agent in situ by reaction with, for example, an alkali metal nitrite. At least 2 moles of hydrogen fluoride will be required as reactants according to the equation:

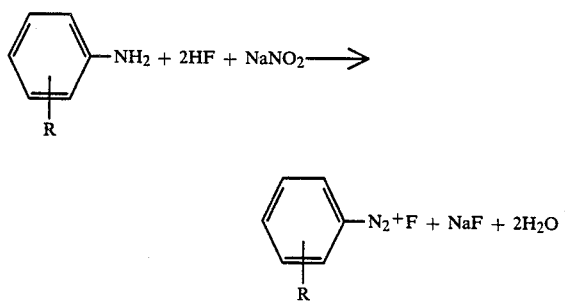

the remainder of the HF (20 to 30 mole) is present as a reaction solvent.

Preferably, the hydrogen fluoride is anhydrous to minimise hydrolysis of the diazotised amine. As some water is formed during diazotisation, hydrolysis may not be completely avoided.

Suitable amines for use in the process of the present invention include amines of the formula (I) :

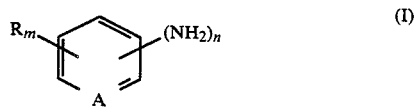

in which A is CH or N; R is halogen, preferably chlorine and fluorine; nitro; alkyl, preferably $C_{1-4}$ alkoxy; trifluoromethyl; hydroxycarbonyl; or alkoxy-carbonyl, preferably $C_{1-4}$ alkoxycarbonyl; m is 0, 1, 2 or 3 and, when m is 2 or 3, the substituents represented by R may be the same or different; and n is 1 or 2.

Examples of suitable aminobenzenes are:
o-, m- and p-toluidine aniline
o-, m- and p-haloaniline
2,4- and 2,5-dimethylaniline
m- and p-alkoxyaniline
m- and p-nitroaniline
m- and p-carboxyaniline and especaally o-carboxyaniline (anthranilic acid)
2-methyl-5-nitroaniline
4,4'-diaminodiphenylethane Illustrative compounds of the pyridine series include 2,3 and 4-aminopyridine, haloaminopyridines such as 2-amino-4,5 and 6-halopyridine and 3-amino-5 and 6-haolpyridine alkylaminopyridines such as 2-amino-4,5 and 6-methyl-pyridine and 2-amino-4, 6-dimethylpyridine.

The invention is illustrated by the following Examples in which percentages are by weight and the abbreviation HPLC means high performance liquid chromatography.

EXAMPLE 1

Preparation of benzene diazoniumfluoride-2-carboxylate

This is carried out in a 300 ml, magnetically stirred vessel fabricated from polypropylene; the vessel is vented through a Drikold-acetone-cooled cold finger-type condenser of polypropylene and provided with a charge port and a thermocouple pocket.

The vessel is chilled to about −5° C. and 100 ml of anhydrous hydrogen fluoride is charged. The contents of the vessel are then stirred magnetically as 18 grams of anthranilic acid is charged over 20 minutes; the temperature is held in the range −5° C. to 0° C. by external cooling. After the anthranilic acid addition is complete the solution is stirred for 10 minutes at −2° C. then addition of 9.4 g of sodium nitrite is commenced and carried out over 45 minutes. The temperature is again maintained in the range −5° C. to 0° C. After completion of the addition, the mixture is stirred for 30 minutes at 0° C. after which the solution of benzen diazoniumfluoride-2-carboxylate is ready for use.

EXAMPLE 2

Preparation of 2-fluoro-benzoic acid

The solution produced in Example 1 above is transferred to a pre-chilled 300 ml autoclave fabricated in Inconel which is sealed and heated to 80° C. and held at 80° C. for 6 hours after which it is cooled and vented. The maximum pressure reached is 250 p.s.i. The autoclave contents are discharged into excess of crushed ice and when all is melted the aqueous mixture is extracted with dichloromethane (250 ml then 2×100 ml). The extracts are evaporated and the residues analysed by HPLC.

The analysis is:

|  | Weight | Analysis | Yield (%) |
| --- | --- | --- | --- |
| First extract | 17.6 g | 92.8/2-FBA | 88.8 |
| Second and third extracts | 1.1 g | 90.8/2-FBA | 5.4 |
|  |  |  | 94.2% |

EXAMPLE 3-7

In the same way as described in example 1 the amines listed in the table below were diazonium using the ratio of anhydrous HF to amine as shown in the Table.

The diazonium fluoride solutions thus obtained were decomposed to yield the corresponding fluoroaromatic compounds by the same method as described in Example 2. The temperature and pressure conditions and yields are as shown in the Table.

TABLE I

| EXAMPLE NO | AMINE | HF RATIO | DECOMPOSITION TEMPERATURE °C. | MAXIMUM PRESSURE p.s.i | PRODUCT | YIELD % |
|---|---|---|---|---|---|---|
| 3 | H₂N-C₆H₄-CH₂-C₆H₄-NH₂ (4,4'-diaminodiphenylmethane) | 33:1 | 60 | 410 | F-C₆H₄-CH₂-C₆H₄-F (4,4'-difluorodiphenylmethane) | 77.6 |
| 4 | 4-methylaniline (NH₂, CH₃) | 25:1 | 45 | 240 | 4-fluorotoluene (F, CH₃) | 71.4 |
| 5 | 2-methyl-5-nitroaniline (NH₂, CH₃, NO₂) | 25:1 | 65 | 270 | 2-fluoro-4-nitrotoluene (F, CH₃, NO₂) | 69.5 |
| 6 | 2-fluoroaniline (NH₂, F) | 25:1 | 110 | 410 | 1,2-difluorobenzene (F, F) | 27.9 |
| 7 | 3-aminopyridine (NH₂, N) | 25:1 | 55 | 295 | 3-fluoropyridine (F, N) | 24.7 |

EXAMPLE 8

An attempt was made to pepare 1,2-difluorobenzene from 2-fluoroaniline by a method similar to that employed by Ferm and VanderWerf with the difference that water was added to the hydrogen fluoride solvent to give a strength of 90% and enable a higher temperature to be attained.

A mixture of hydrogen fluoride (135 g; 6.75 mol) water (15 g) and 2-fluoroaniline (20 g; 0.18 mol) was prepared and cooled to −20° C. whereupon sodium nitrite (13.1 g; 0.19 mol) was added over 30 minutes. The temperature was maintained at −20° C. by control of the addition rate and the use of external cooling. When the nitrite addition was complete the mixture was kept for a further 30 minutes at the same temperature and then gently warmed up to distil the contents slowly over 4.5 hours. The maximum internal temperature reached was 88.5° C. The tarry residue and the colourless homogeneous distillate were both extracted with methylene chloride and the extracts were examined by capillary gas chromatography. No 1,2-difluorobenzene was seen in either extract.

We claim:

1. A process for the preparation of a fluoroaromatic or fluoroheterocyclic compound, which comprises diazotising the corresponding amino-aromatic or amino-heterocyclic compound in hydrogen fluoride and decomposing the diazonium salt in the diazotisation mixture so formed, characterised in that decomposition is carried out at super atmospheric pressure.

2. A process according to claim 1 wherein the decomposition is carried out at pressure in the range 70–200 psig.

3. A process according to claim 2 wherein the decomposition is carried out at pressure in the range 80–100 pisg.

4. A process according to claim 3 wherein the decomposition is carried out at pressure in the range 85–95 psig.

5. A process according to claim 4 wherein the decomposition is carried out at a pressure of 90 psig.

6. A process according to claim 1 wherein the decomposition is carried out at pressure in the range 200 to 500 psig.

7. A process according to claim 6 wherein the decomposition is carried out at pressure in the range 200 to 300 psig.

8. A process according to claim 7 wherein the decomposition is carried out at pressure in the range 20 to 280 psig.

9. A process according to claim 8 wherein the decomposition is carried out at a pressure of substantially 250 psig.

10. A process according to claim 1 wherein the corresponding amino-aromatic or amino-heterocyclic compound is an amine of the formula (I):

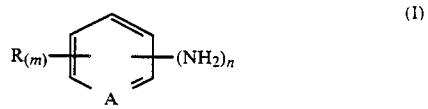

in which A is CH or N; R is halogen, nitro; alkyl; alkoxy; trifluoromethyl; hydroxycarbonyl; or alkoxycarbonyl; m is 0, 1, 2 or 3 and, wherein m is 2 or 3, the substituents represented by R may be the same or different; and n is 1 or 2.

11. A process according to claim 10 wherein the corresponding amino-aromatic or amino-heterocyclic compound is o-, m-, or p-haloaniline, 2,4- and 2,5-dimethylaniline m- or p-alkoxyaniline, m- or p-nitroaniline m- or p-carboxyanilime and especially 0-carboxy aniline, 2-methyl-5nitroaniline, 4,4'-diamino-diphenylmethane, o-, m- or p-toludine, aniline, 2,3 and 4-aminopyridine, 2-amino-4,5 and 6-halopyridine, 3 amino-5 and 6-halopyridine, 2-amino-4,5 and 6-methyl pyridine or 2-amino-4,6-dimethyl pyridine.

12. A process for the preparation of 2-fluorobenzoic acid which comprises diazotizing the corresponding amino-aromatic or amino-heterocyclic compound in hydrogen fluoride and decomposing the diazonium salt in the diazotisation mixture so formed, characterised in that decomposition is carried out at super atmospheric pressure.

13. A process according to claims 10 or 12 wherein the decomposition is carried out at a temperature in the range of 40° C. to 100° C.

14. A process according to claim 13 wherein the decomposition is carried out at a temperature in the range of 60° C. to 100° C.

15. A process according to claim 14 wherein the decomposition is carried out at a temperature in the range 75° C. to 85° C.